US00PP12340P2

(12) United States Plant Patent

Cosner et al.

(10) Patent No.: US PP12,340 P2
(45) Date of Patent: Jan. 8, 2002

(54) IMPATIENS PLANT NAMED 'TITAG'

(76) Inventors: Harlan B. Cosner; Susan L. Cosner, both of P.O. Box 173, Broadbent, OR (US) 97414

( * ) Notice: Subject to any disclaimer, the term of this patent is extended or adjusted under 35 U.S.C. 154(b) by 0 days.

(21) Appl. No.: 09/536,168

(22) Filed: Mar. 23, 2000

(51) Int. Cl.[7] ..... A01H 5/00
(52) U.S. Cl. ..... Plt./317
(58) Field of Search ..... Plt./317, 319

(56) References Cited

U.S. PATENT DOCUMENTS

P.P. 3,918 * 6/1976 Hope et al. ..... Plt./317
P.P. 10,256 * 2/1998 Cosner et al. ..... Plt./317
P.P. 11,533 * 9/2000 Jonkers ..... Plt./317
P.P. 11,590 * 10/2000 Jonkers ..... Plt./317

OTHER PUBLICATIONS

UPOV–ROM GTITM Computer Database, 2000/04, GTI Jouve Retrieval Software, citation for 'TiTag'.*

* cited by examiner

*Primary Examiner*—Bruce R. Campell
*Assistant Examiner*—Susan B. McCormick
(74) *Attorney, Agent, or Firm*—Bradley M. Ganz, Esq.

(57) ABSTRACT

A new an distinct cultivar of *Impatiens walleriana* plant as illustrated named 'TiTag', characterized by moderately strong peduncles and pedicels, large flowers, fully double and symmetrical, very bright orange colored flowers, strong stems, flowers that are positioned above or beyond the foliage, good heat tolerance, dark green foliage and mounded, freely branching and dense plant habit.

1 Drawing Sheet

BACKGROUND—FIELD OF INVENTION

The present invention relates to a new and distinct cultivar botanically known as *Impatiens walleriana*, and by the cultivar name 'TiTag'.

The cultivar of the photograph was developed and selected in a controlled breeding program in a controlled environment in Broadbent, Oreg. by the inventors, Harlan Cosner and Sue Cosner, as described herein.

BACKGROUND—DESCRIPTION OF THE PRIOR ART

The closest known cultivar of prior art is named '*Tropical Orange*', subject of U.S. Plant Pat. No. 9,610.

COMPARISON

The impatiens plant of the present invention differs from prior plants, namely '*Tropical Orange*' in at least the following ways:

1. the plant of the present invention has been shown to perform better in the heat than '*Tropical Orange*';
2. the flowers of the present invention have been shown to have more stable coloring than the flowers of '*Tropical Orange*', which had instability in flower color ranging from orange to soft salmon, and variegated orange/soft salmon colored flowers;
3. the present cultivar have been shown to have darker foliage than that of '*Tropical Orange*';
4. the present cultivars have been shown to have stronger stems than those of '*Tropical Orange*'; and
5. the peduncles and pedicels of the present impatiens plants are stronger than those of '*Tropical Orange*'. The weaker peduncles and pedicels on '*Tropical Orange*' cause the flowers to droop slightly to moderately.

These and other characteristics will be apparent to persons skilled in the art.

The present cultivar was developed by standard cross-pollination. Its seed parent has semi-double orange flowers. This plant was designated B-9X-11 under the inventors' controlled breeding program. The pollen parent has semi-double orange flowers. This plant was designated B-9X-1300 under the inventors' controlled breeding program. The parent plants are not the subject of any granted patent or pending application. The cross was made in the inventors' controlled breeding program, and the first asexual reproduction was made at Coquille, Oreg. Successive asexually reproduced generations have shown the present invention to be stable. Each asexually reproduced generation has been accomplished using lateral stems with leaves.

The traits of the cultivar of the present invention that have been observed in each successive generation of asexual reproduction and which are unique, are moderately strong peduncles and pedicels, large flowers, fully double and symmetrical, very bright orange colored flowers, strong stems, flowers that are positioned above or beyond the foliage, dark green foliage and mounded, freely branching and dense plant habit, and both male and female sterility.

Color references are according to The Royal Horticultural Society Colour Chart, except where general terms of ordinary dictionary significance are used.

DETAILED DESCRIPTION

The following observations, measurements and description of the plants and flowers are based on the environmental and cultural practices at Coquille, Oreg. The following measurements, values and comparisons describe plants grown under a double layer of polyethylene film with temperatures typically ranging from about 55° F. to about 85° F. during the daytime. Night heat was provided by bench top set at 62° F. The individual plants were grown in six-inch Azalea containers in a soiless medium. Plants were liquid fed with high nitrate plus trace elements applied at N level 150 PPM of two successive feedings followed by one leaching of clear water. Plants started in the last week of June and finished in late September and grown at light levels between 4,000 and 6,000 ft. candles.

The plant of the present invention has not been observed in all possible environmental and/or cultural conditions. The phenotype may vary significantly with variations in environment such as temperature, light level, humidity and also with cultural practices such as fertility, soil and water quality.

The accompanying photograph illustrates the overall appearance and the flower color of the cultivar of the present invention described herein. The photograph was taken of a mature plant 14 weeks of age, during full inflorescence. There may be variations between the colors in the photograph and the colors in the following description due to light reflectance, or the amount of blue or red light captured in the film. If such variations occur, the written description shall control.

Parentage: The new cultivar was developed by standard cross-pollination. As noted above, its seed parent was a semi-double with orange flowers. Its pollen parent was a semi-double with orange flowers.

Propagation:

*Type cutting.*—Lateral tips of plants were the cuttings used for asexual reproduction.

*Time to initiate roots.*—Approximately 7 to 14 days at 72° F. soil temperature.

Appearance and form of plant:

*Plant form and habit.*—Mounded to prostrate mounded, with a medium vigorous, dense and bushy growing habit.

*Plant size.*—Height is about 24 cm and width is about 45 cm.

*Root description.*—The rooting habit is characterized by numerous, fibrous and well-branched roots.

*Branching habit.*—Plants are self-branching. Stems are strong and freely produced. The number of stems depends upon cultural practices, age of stems used as cuttings and the number of growth buds present on the cutting when stuck. The average stem length is about 22.5 cm. Each stem generally produces about three laterals.

*Stems.*—Diameter is about 0.5 cm, and become larger with age. Internode length is about 2.75 cm. Color is 146B to 146C with markings close to 178A. The observed plant's stem texture is smooth.

*Foliage.*—Leaves are simple, generally symmetrical, abundant, alternate and flat. Shape is ovate with attenuate base, acuminate apex, and crenate margin. Texture is smooth and satiny. The observed plant's leaf venation pattern is similar to other plants having similar leaf shapes, with single veins branching upwardly off from the central, longitudinal axis of each leaf, along the length of the axis, toward the margin of the leaf and forming an acute angle relative to the axis.

*Foliage size.*—Size of the largest leaves is about 7 cm in length, and 4.5 cm in width.

*Foliage color.*—Adaxial color is darker than 147A, venation is 146A. Abaxial is close to 148B with markings close to 177A, venation is close to 146A with reddish markings close to 178B.

*Petioles.*—Each petiole is half round with a top surface width of about 3 mm, a depth of about 1.5 mm and a length of about 1.5 cm. Color on the bottom surface is 146B, the top surface is close to 148B to 148C with reddish markings close to 178B.

*Flower size.*—The largest flowers have a diameter of about 5.5 cm, a depth of about 2.25 cm.

*Flower texture.*—The flower texture is smooth and satiny.

*Flower count.*—12 or more per stem from buds to open flowers at any time during the flowering period.

*Flower fragrance.*—No discernible fragrance.

*Natural flowering season.*—Year around under greenhouse conditions, and the frost-free period from spring through fall outdoors.

*Duration of flowering.*—Continuous throughout the flowering season.

*Time to flower.*—About six weeks from a rooted cutting.

*Buds.*—Buds are ovate in shape with a length of about 1.1 cm, a width of about 1 cm and a depth of about 1 cm. Bottom color close to 146C to 146D. Top is 146C with blotches close to 178B.

*Petal size and shape.*—The largest petals generally consist of two petals fused at base, overlapping at center, each being about 2.5 cm in length and about 2.7 cm in width. Shape is obovate to exaggerated obovate with attenuate base, entire margin, obtuse to retuse apex.

*Petal color.*—Adaxial color is close to 33A at the center and 40A toward edges. Abaxial color is closest to 40C with spots at center toward base close to 193C to 193D.

*Petal count.*—Numerous, generally 25 or more.

*Spur.*—Shape is a curved acicular tube about 4 cm. in length, and about 3 mm. in diameter at sepal end, tapering to a point at the apex. Color is close to 199B at the base, darkening to close to 183A at the apex.

*Calyx.*—The calyx consists of a single sepal. The size of largest is about 1 cm. long and about 1 cm. wide. Abaxial color is 193A. Adaxial surface color is 193B with a blotch at base close to 181C.

*Peduncles.*—Length is about 2 cm. and diameter is about 2 mm. Color is 146B with reddish hard to determine tiny streaks which appear close to 187C. Peduncles have a smooth texture.

*Pedicels.*—Usually number 2 or 3 with a length of about 2 cm. and diameter is about 2 mm. Color is 146B with reddish hard to determine tiny streaks which appear close to 187C. Pedicels have a smooth texture.

*Reproductive organs.*—The plants of the new cultivar are both male and female sterile. No reproductive organs have been found to exist.

*Disease resistance.*—Plants have shown good resistance to botrytis.

*Rooting ability.*—Easy, no hormones are required.

*Cold/heat resistance.*—'TiTag' was grown side by side with '*Tropical Orange*' in temperatures of daytime highs of about 90° F. '*Tropical Orange*' had weak stems, causing the plant to fall over, the peduncles were weak and could not properly support the flowers in a face-out position, and the color was faded and unstable. 'TiTag' showed strong peduncles keeping the flowers positioned face out, the color was bright and clear the plant maintained a nice mounded appearance, and its flowers were larger than the flowers of '*Tropical Orange*'.

What is claimed:

1. A new and distinct cultivar of *Impatiens walleriana* plant as illustrated and as described herein.

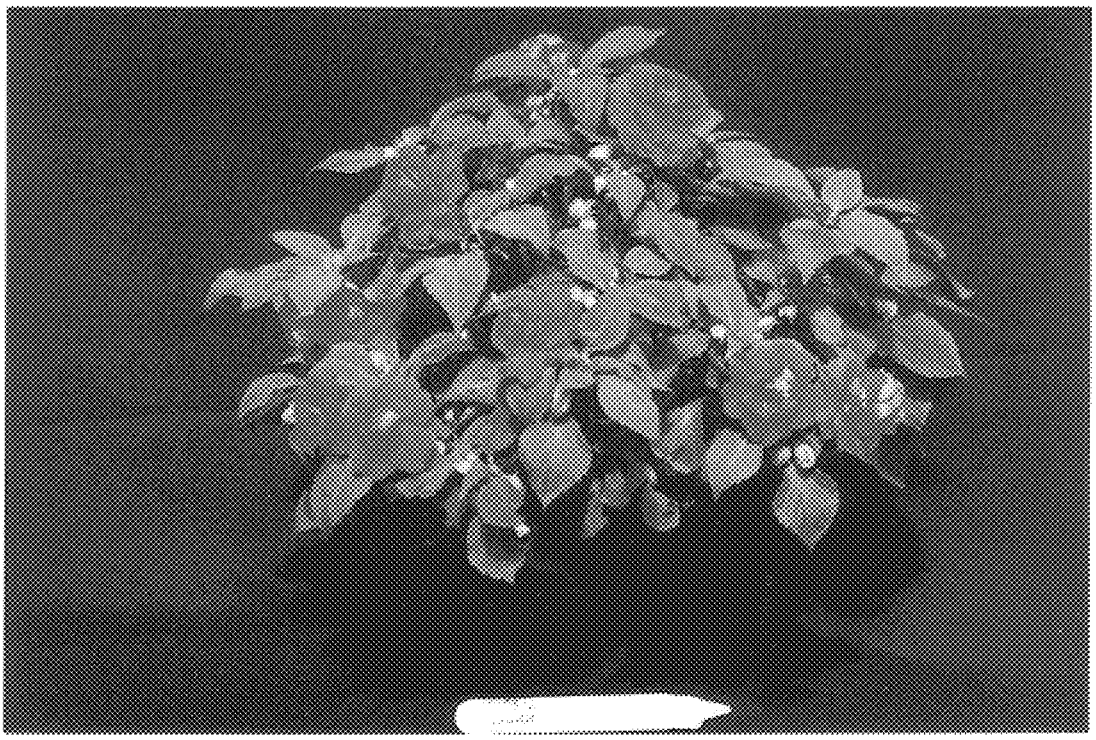

* * * * *